United States Patent
Schade et al.

(10) Patent No.: US 10,184,888 B2
(45) Date of Patent: Jan. 22, 2019

(54) DEVICE AND METHOD FOR DETERMINING A REFRACTIVE INDEX

(71) Applicants: Fraunhofer-Gesellschaft zur Förderung der angewandten Forschung e.V., Munich (DE); Boston University, Boston University, MA (US)

(72) Inventors: Wolfgang Schade, Goslar (DE); Jörg Burgmeier, Osterode (DE); Anna Lena Baumann, Goslar (DE); Björn Reinhard, Brookline, MA (US)

(73) Assignees: FRAUNHOFER-GESELLSCHAFT ZUR FÖRDERUNG DER ANGEWANDTEN FORSCHUNG E.V., Munich (DE); TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/515,958

(22) PCT Filed: Oct. 1, 2015

(86) PCT No.: PCT/EP2015/072653
§ 371 (c)(1),
(2) Date: Mar. 30, 2017

(87) PCT Pub. No.: WO2016/050895
PCT Pub. Date: Apr. 7, 2016

(65) Prior Publication Data
US 2017/0307521 A1 Oct. 26, 2017

(30) Foreign Application Priority Data
Oct. 2, 2014 (DE) .................. 10 2014 220 040

(51) Int. Cl.
*G01N 21/41* (2006.01)
*G01N 21/552* (2014.01)
(Continued)

(52) U.S. Cl.
CPC ....... *G01N 21/412* (2013.01); *G01N 21/4133* (2013.01); *G01N 21/552* (2013.01);
(Continued)

(58) Field of Classification Search
CPC ......... G01N 2021/7776; G01N 21/412; G01N 21/552; G01N 21/77; G01N 21/4133;
(Continued)

(56) References Cited

U.S. PATENT DOCUMENTS 7,813,599 B2  10/2010  Moore
2006/0013523 A1  1/2006  Childers et al.
(Continued)

FOREIGN PATENT DOCUMENTS

EP  1 195 582 A1  4/2002
GB  2 447 966 A  10/2008
WO  WO 2014/118519 A1  1/2014

OTHER PUBLICATIONS

International Search Report with translation, issued in International Patent Application No. PCT/EP2015/072653, dated Dec. 10, 2015, pp. 1-7, European Patent Office, Rijswijk, The Netherlands.
(Continued)

*Primary Examiner* — Tri T Ton
(74) *Attorney, Agent, or Firm* — Brinks Gilson & Lione

(57) ABSTRACT

A device for determining a refractive index may be provided. The device including at least one waveguide having a core and a cladding surrounding the core, the cladding being at least partly removed in at least one first longitudinal portion and the core including at least one fiber Bragg grating in at least one second longitudinal portion. A method
(Continued)

for determining a refractive index or a pressure change in a fluid may also provided. The method may include at least one waveguide having a core and a cladding surrounding the core, the cladding being at least partly removed in at least one longitudinal portion. A method for producing such a device may also be provided.

18 Claims, 4 Drawing Sheets

(51) Int. Cl.
*G01N 21/77* (2006.01)
*G01V 1/18* (2006.01)

(52) U.S. Cl.
CPC ............ *G01N 21/554* (2013.01); *G01N 21/77* (2013.01); *G01N 21/774* (2013.01); *G01V 1/18* (2013.01); *G01N 2021/7776* (2013.01)

(58) Field of Classification Search
CPC ...... G01N 21/554; G01N 21/774; G01V 1/18; G01V 1/186
USPC .................................. 356/128–137
See application file for complete search history.

(56) References Cited

U.S. PATENT DOCUMENTS

| | | | |
|---|---|---|---|
| 2009/0217769 A1 | 9/2009 | Roberts | |
| 2010/0259752 A1* | 10/2010 | Shah | B82Y 20/00 356/300 |
| 2011/0085759 A1* | 4/2011 | Lee | G01N 21/7703 385/12 |

OTHER PUBLICATIONS

Jörg Burgmeier, et al., "Plasmonic nanoshell functionalized etched fiber Bragg gratings for highly sensitive refractive index measurements" dated Feb. 9, 2015, pp. 546-549, available in Optics Letters vol. 40, No. 4. © 2015 Optical Society of America.

Lai-Kwan Chau et al. "Fiber-optic chemical and biochemical probes based on localized surface plasmon resonance" dated Mar. 9, 2005, pp. 101-105, Sensors and Actuators B 113 (2006), © 2005 Elsevier B.V.

Michael C. Emmons et al. "Magneto-optic field coupling in optical fiber Bragg gratings," dated Mar. 31, 2012, pp. 157-160, Optical Fiber Technology 18 (2012), © 2012 Elsevier Inc.

G Laffont et al. "Tilted short-period fibre-Bragg-grating-induced coupling to cladding modes for accurate refractometry" dated Mar. 1, 2001, pp. 765-770, Meas. Sci. Technol. 12 (2001), © 2001 IOP Publishing Ltd.

Wei Liang et al. "Highly sensitive fiber Bragg grating refractive index sensors" dated Apr. 8, 2005, pp. 1-4, Applied Physics Letters 86, 151122 (2005) © 2005 American Institute of Physics.

V.V.R. Sai et al. "Novel U-bent fiber optic probe for localized surface plasmon resonance based biosensor", dated Feb. 20, 2009, pp. 2804-2809, Biosensors and Bioelectronics 24 (2009), © 2009 Elsevier B.V.

Kerstin Schroeder et al. "A fibre Bragg grating refractometer" dated Apr. 17, 2001, pp. 757-765,Meas. Sci. Technol. 12 (2001), © 2001 IOP Publishing Ltd.

Bannur Nanjunda Shivananju et al. "Highly Sensitive Carbon Nanotubes Coated Etched Fiber Bragg Grating Sensor for Humidity Sensing" dated Aug. 8, 2014, pp. 2615-2619, IEEE Sensors Journal vol. 14 No. 8, © 2014 IEEE.

* cited by examiner

DEVICE AND METHOD FOR DETERMINING A REFRACTIVE INDEX

CROSS REFERENCE TO RELATED APPLICATIONS

This application is a 371 nationalization of PCT/EP2015/072653, entitled "Device and method for determining a refractive index," having an international filing date of Oct. 1, 2015, the entire contents of which are hereby incorporated by reference, which in turn claims priority under 35 USC § 119 to German patent application 10 2014 220 040.7 filed on Oct. 2, 2014, the entire contents of which are hereby incorporated by reference.

TECHNICAL FIELD

The invention relates to a device for determining a refractive index, which contains at least one waveguide having a core and a cladding surrounding the core, the cladding being at least partly removed in at least one first longitudinal portion and the core containing at least one fiber Bragg grating in at least one second longitudinal portion. The invention also relates to a method for determining a refractive index or a pressure change in a fluid, which uses at least one waveguide having a core and a cladding surrounding the core, the cladding being at least partly removed in at least one longitudinal portion. Finally, the invention relates to a method for producing such a device.

BACKGROUND

W. Liang, Y. Huang, Y. Xu, R. K. Lee and A. Yariv: "Highly Sensitive Fiber Bragg Grating Refractive Index Sensors", Appl. Phys. Lett. 86, 151122 (2005) discloses a fiber-optic sensor which contains a Bragg grating. The fiber-optic sensor contains an optical waveguide having a core and a cladding, the cladding being removed in the Bragg grating region. The sensor can be immersed into gases or liquids, the Bragg wavelength reflected by the Bragg grating changing in accordance with the index of refraction or the refractive index of the medium surrounding the sensor.

However, a drawback of this sensor is the low resolution thereof. The Bragg wavelength will merely change by fractions of a nanometer when the refractive index changes. As a result, highly complex light sources and spectrometers are required to determine the wavelength shift and the resulting refractive index of the medium.

BRIEF DESCRIPTION OF THE DRAWINGS

There are shown in.

DETAILED DESCRIPTION

Figure 1:
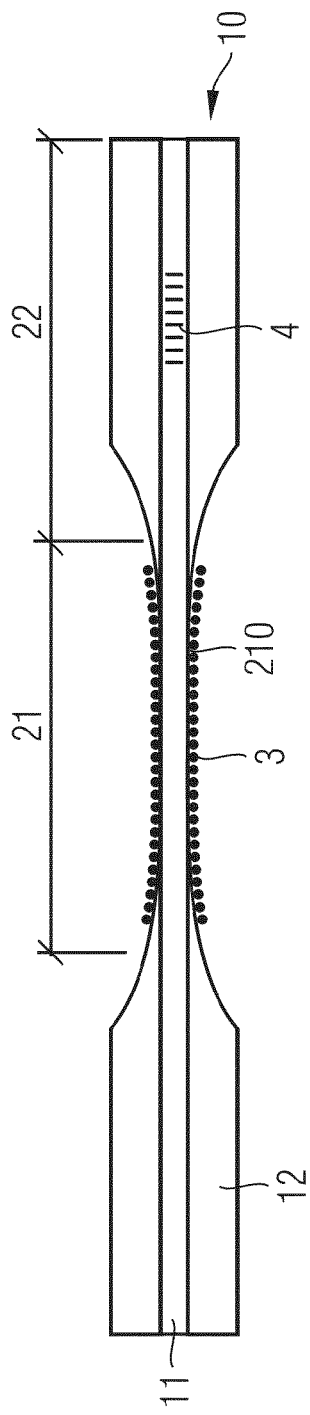
FIG. 1 a first embodiment of the device according to the invention.

Proceeding from the prior art, the object of the invention is therefore to provide a method and a device for determining a refractive index, which can be operated with little effort and supplies more precise results.

The invention proposes to use a waveguide having a core and a cladding surrounding the core in order to determine a refractive index of a fluid. In some embodiments of the invention, the waveguide can consist of glass or a plastic material. In some embodiments of the invention, it is possible to use a generally known glass fiber from telecommunications and/or optical communications engineering. A geometrically defined interface can be formed between core and cladding and can delimit the material of the core from the material of the cladding. The index of refraction between core and cladding is chosen in such a way that light propagating in the core can be totally reflected at the interface between core and cladding so as to guide the light in the core.

The fluid can be selected from a gas and/or a liquid.

The device according to the invention has at least one first longitudinal portion, in which the cladding is at least partly removed. The partial removal of the cladding can be done in such a way that the cladding is removed in individual sub-portions of the first longitudinal portion and is not removed in other sub-portions. In other embodiments of the invention, the first longitudinal portion of the cladding can be thinner than along the remaining length of the waveguide without fully removing the cladding in the first longitudinal portion. In yet other embodiments of the invention, the cladding can be fully removed in the first longitudinal portion, as a result of which the interface between core and cladding in the first longitudinal portion forms the outer surface of the waveguide. In some embodiments of the invention, a plurality of first longitudinal portions can be present, as a result of which it is possible to measure a refractive index or a pressure fluctuation, e.g. a switch signal, at various locations along the waveguide.

The waveguide according to the invention contains at least one fiber Bragg grating. The Bragg grating contains a plurality of spatial regions which have an index of refraction that differs from the adjoining material of the core. The modified spatial regions can have a constant distance from one another, which defines the grating constant of the fiber Bragg grating. In other embodiments of the invention, the distance can be variable, thus forming a chirped fiber Bragg grating. The effect of the fiber Bragg grating, or abbreviated Bragg grating, is that a part of the electromagnetic spectrum which is defined by the grating constant is reflected whereas light of different wavelengths can pass through the Bragg grating. The reflected wavelength and/or the reflected wavelength range is referred to as Bragg wavelength. Bragg gratings can be obtained e.g. by point-to-point exposure of the core by means of laser radiation, in particular radiation of a short-pulse laser.

The invention now proposes to provide at least one partial area of the surface in the first longitudinal portion with nanoparticles. The effect of this feature is that intensity losses of the wave reflected by the Bragg grating occur. These losses are dependent on the refractive index of the medium surrounding the first longitudinal portion. Two effects are responsible for these intensity losses that are dependent on the refractive index. On the one hand, the evanescent portion of the guided light is dependent on the refractive index, as a result of which more or less light can interact with the nanoparticles in accordance with the surrounding medium. Furthermore, the scattering and absorbing properties of the nanoparticles as such are dependent on the refractive index of the surrounding medium. The fiber Bragg grating according to the invention enhances the intensity losses, thus rendering possible the measurement in reflection, as a result of which the instruments needed for the operation of the device are reduced.

The invention proposes not to determine, or not to determine exclusively, the shift of the Bragg wavelength but the intensity of reflected light in order to determine the refractive index of a medium surrounding the device. It was found that the losses in accordance with the refractive index render possible a much more distinct measurement signal than the comparatively small shift of the Bragg wavelength. As a result, the measurement can be carried out with increased accuracy and an intensity measurement is possible with relatively little effort compared to the determination of the wavelength, e.g. of an individual photodiode, the output voltage of which is proportional to the incident light intensity.

In some embodiments of the invention, the second longitudinal portion can form at least part of the first longitudinal portion. This means that the Bragg grating is also arranged in a portion of the waveguide, in which the cladding is at least partly removed. As a result, the intensity loss of the optical signal guided in the core can be increased in such a way that the signal-to-noise ratio of the measurement is improved.

In some embodiments of the invention, periodic holes can be present in the cladding adjacent to the fiber Bragg grating. It has turned out that following the production of the Bragg grating by exposing the core to laser radiation, part of the cladding which lies in the beam path is also modified by the laser radiation in such a way that it is preferably removed by wet or dry chemical etching. Therefore, it is possible to selectively remove the part of the cladding which borders directly on the Bragg grating. Since the cladding in the remaining regions remains fully or at least almost fully intact, the waveguide largely retains its original properties, wherein a very large interaction cross-section for scatter and absorption can simultaneously occur between the light guided in the waveguide and the nanoparticles. In addition, the nanoparticles can be deposited as clusters in the periodic holes, as a result of which the plasmon resonance of the nanoparticles can be adjusted by the size of the clusters.

In some embodiments of the invention, the waveguide can be made as a single mode fiber. This means that merely a single mode is guided in the core. This also keeps constant the mode distribution even when the form of the waveguide changes, as a result of which the measurement signal is available with increased stability and the measurement accuracy is thus increased.

In some embodiments of the invention, the nanoparticles can contain, or consist of, a metal or an alloy and have a plasmon frequency which corresponds approximately to a resonance frequency of the Brag grating. The plasmon frequency can in this connection be adjusted by the composition of the nanoparticles, the size of the nanoparticles and the size of the clusters adhering to the surface of the waveguide. Since the plasmon frequency is matched with the Bragg wavelength, the losses can be increased and the measurement accuracy is raised.

In some embodiments of the invention, the nanoparticles can contain, or consist of, palladium. In some embodiments of the invention, the nanoparticles can be activated, e.g. by a plasma treatment or a coating deposited on the nanoparticles. As a result, predeterminable molecules can be attached to the nanoparticles, thus changing the plasmon frequency. Therefore, the device according to the invention does not only allow the determination of the refractive index of the surrounding medium but also the measurement of the concentration of one or more target molecules.

In some embodiments of the invention, at least one partial area of the surface provided with nanoparticles in the first longitudinal portion can additionally carry antibodies. This allows the attachment of predeterminable antigens, viruses or other biological material, as a result of which the concentration of predeterminable antigens or viruses can be determined by means of the light intensity and/or the Bragg wavelength.

In some embodiments of the invention, the measurement signal can be produced by means of at least one laser light source or another narrow-band light source, the emission wavelength of which corresponds approximately to the Bragg wavelength of the fiber Bragg grating. At least one photodiode is available to receive the light and serves to receive light reflected by the Bragg grating. Since in this case no spectrometer is necessary to produce the measurement signal and semiconductor light sources are available as a compact component, the measurement device can be particularly simple and still provide reliable results.

In some embodiments of the invention, the first longitudinal portion can have a length of about 0.1 mm to about 5 mm. In some embodiments of the invention, the first longitudinal portion can have a length of about 0.5 mm to about 2 mm. The refractive index can also be determined in spatially resolved fashion by such miniaturized sensors.

In some embodiments of the invention, an apparatus for determining the wavelength of the light reflected by the fiber Bragg grating can additionally be available. As a result, different measuring locations can be discriminated by wavelength multiplex, or the measurement of the index of refraction can be made plausible and/or carried out with greater accuracy by additional determination of the wavelength shift and the intensity.

In some embodiments of the invention, an apparatus for determining the wavelength can additionally be, or contain, a color filter, e.g. a band-pass, high-pass or low-pass filter. In other embodiments, an apparatus for determining the wavelength can comprise a spectrometer in order to determine the wavelength with greater accuracy.

The invention shall be explained in more detail below by means of drawings without limiting the general inventive concept, wherein:

FIG. 1 shows a first embodiment of the device according to the invention.

Figure 2:
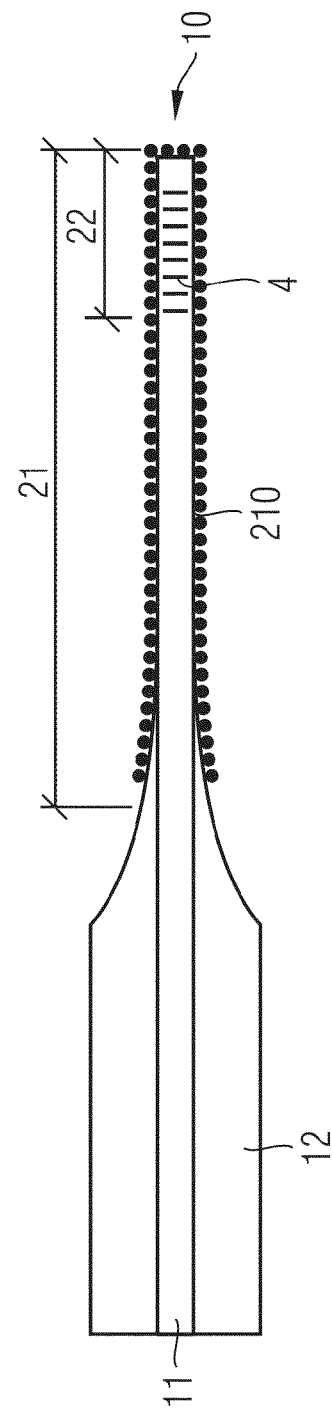
FIG. 2 a second embodiment of the device according to the invention.

FIG. 2 shows a second embodiment of the device according to the invention.

Figure 3:
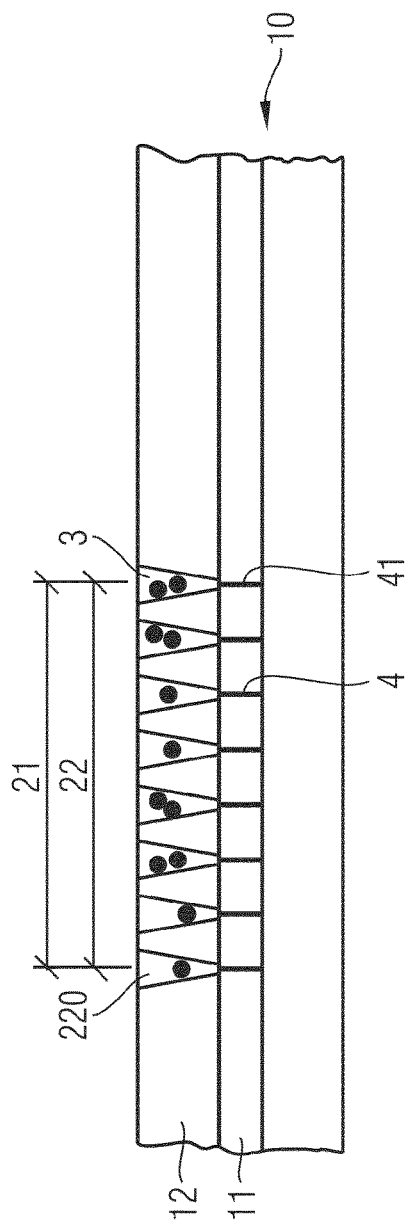
FIG. 3 a schematic representation of a third embodiment of the device according to the invention.

FIG. 3 shows a schematic representation of a third embodiment of the device according to the invention.

Figure 4:
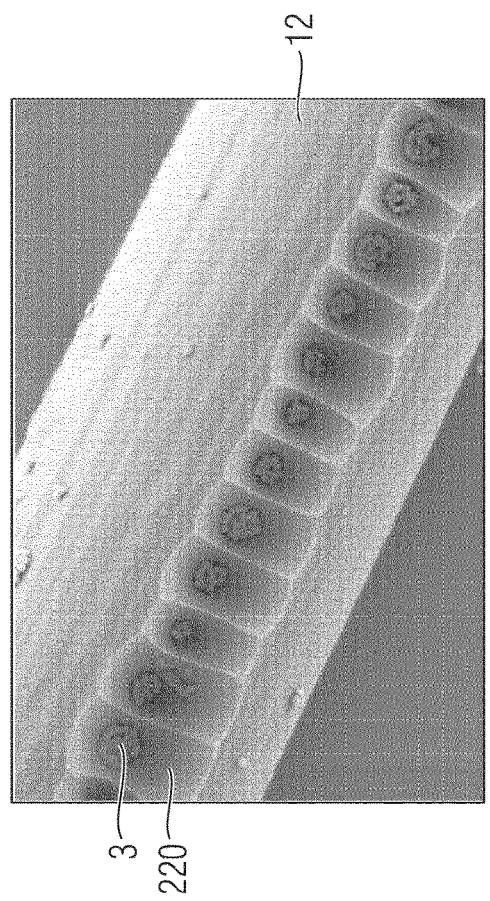
FIG. 4 an electron-microscopic image of the device according to FIG. 3.

FIG. 4 shows an electron-microscopic image of the device according to FIG. 3.

Figure 5:
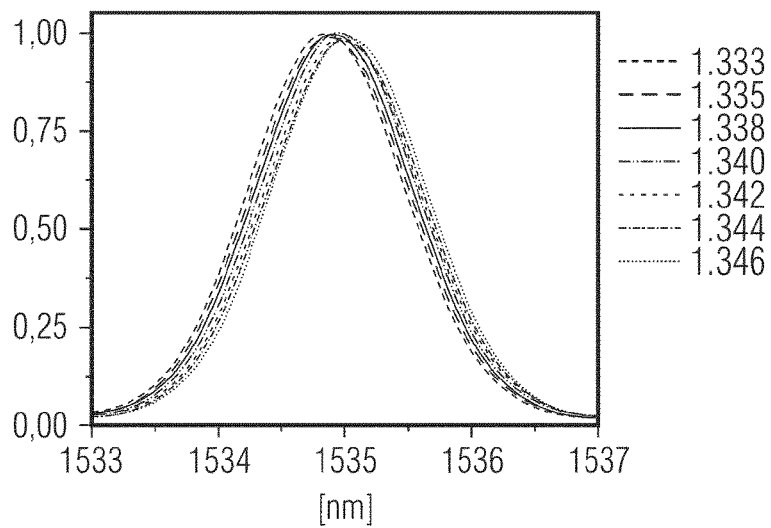
FIG. 5 the change in the Bragg wavelength in accordance with the refractive index.

FIG. 5 shows the change in the Bragg wavelength in accordance with the refractive index.

Figure 6:
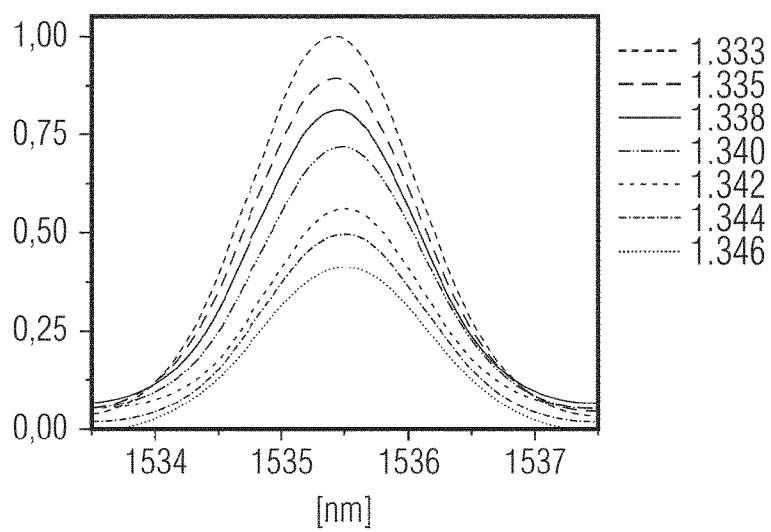
FIG. 6 the intensity in accordance with the refractive index.

FIG. 6 shows the intensity in accordance with the refractive index.

Figure 7:
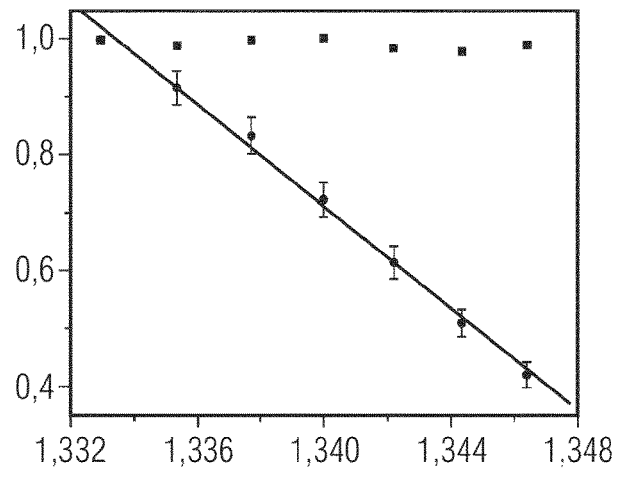
FIG. 7 the influence of the nanoparticles on the optical losses.

FIG. 7 shows the influence of the nanoparticles on the optical losses.

Figure 8:
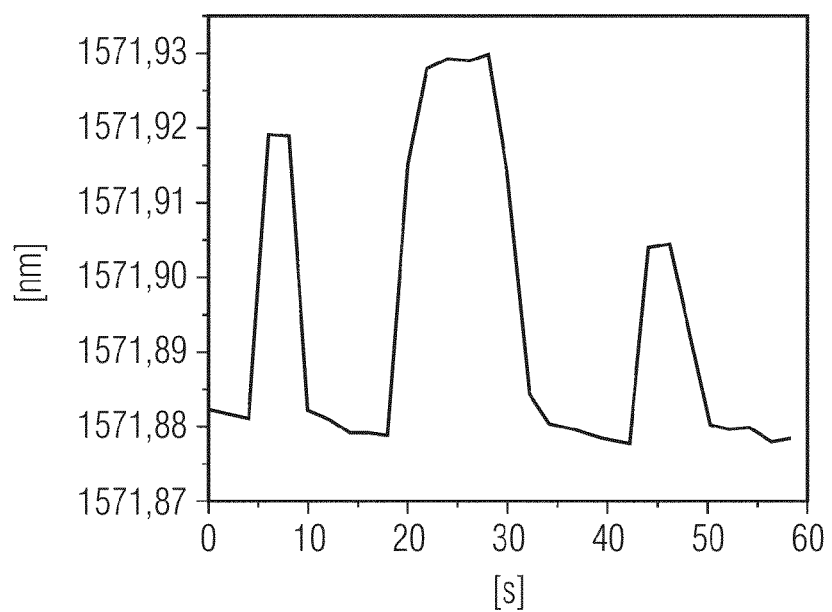
FIG. 8 the use of the device according to the invention as a hydrophone.

FIG. 8 shows the use of the device according to the invention as a hydrophone.

A first embodiment of the present invention is explained by means of FIG. 1. The device for determining a refractive index contains at least one waveguide 10. The waveguide 10 has at least one core 11 and a cladding 12 surrounding the core. The cladding 12 is at least partly removed in at least one first longitudinal portion 21. The at least partial removal can be made, as shown in FIG. 1, by reducing the diameter of the waveguide 10 in such a way that the cladding 12 has a smaller thickness. In some embodiments of the invention, the cladding can be removed up to the interface between core and cladding, such that the surface 210 in the first longitudinal portion 21 is given by the surface of the core 11.

The surface 210 in the first longitudinal portion 21 is at least partly provided with nanoparticles 3. The nanoparticles 3 can be deposited e.g. from an aqueous solution, such that they adhere to the surface 210. In other embodiments of the invention, the nanoparticles can be applied to the surface 210 by a plasma beam. The plasma beam can additionally effect a surface modification and/or an activation of the nanoparticles, as a result of which predeterminable target molecules can attach to the nanoparticles and/or the plasmon frequency of the nanoparticles has a predeterminable value.

The device also has at least one second longitudinal portion 22 which accommodates a Bragg grating 4. The Bragg grating 4 effects that a wavelength or a wavelength region, predeterminable by the grating constant, is reflected in such a way that light on one side of the waveguide 10 can be coupled and decoupled. Therefore, the reflected light passes twice through the first longitudinal portion 21 and can couple to the nanoparticles 3 in evanescent fashion. The intensity losses in the first longitudinal portion 21 are dependent on the index of refraction or the refractive index of the medium surrounding the waveguide 10, as a result of which the intensity decoupled from the waveguide 10 is smaller than the coupled intensity. The identified intensity is thus a measure of the refractive index.

The first longitudinal portions 21 and second longitudinal portions 22, all shown in FIG. 1, can be available several times along the length of the waveguide 10, as a result of which the refractive index can be measured at several locations at the same time. In this connection, the measuring location can be determined by means of the Bragg wavelength of the respective Bragg grating 4.

A second embodiment of the invention is explained by means of FIG. 2. Equal components of the invention are provided with equal reference signs, and therefore the description is limited to the essential differences.

As is shown in FIG. 2, the second longitudinal portion 22, which contains at least one Bragg grating 4, consists of part of the first longitudinal portion 21, in which the cladding 12 is at least partly removed and the surface 210 of which is provided with nanoparticles 3. The effect of this feature is that the Bragg grating does not only allow the measurement in reflection but also enhances the intensity losses on the surface 210. Due to the Bragg grating 4, a major part of the light guided in the core 11 can interact with the nanoparticles 3, thus rendering possible a more precise determination of the refractive index.

It is alternatively or additionally possible to determine the Bragg wavelength which also changes in accordance with the index of refraction or the refractive index of the medium surrounding the waveguide 10. As a result, the values obtained from the measurement of the intensity can be made plausible.

FIG. 3 and FIG. 4 explain a third embodiment of the device according to the invention. In this connection, FIG. 3 shows a section through the waveguide 10, and FIG. 4 shows an electron-microscopic image of the outer side of the waveguide.

In the third embodiment, the Bragg grating 4 is produced in generally known manner by point-to-point exposure using a short-pulse laser in the core 11 of the waveguide 10. The laser radiation modifies the material of the core 11 in the intensity maximum in such a way that spatial regions 41 are formed, which have a different index of refraction than adjacent regions of the core 11. The illustrated embodiment shows by way of example 8 spatial regions 41, which are inserted into the core 11 in equidistant fashion. In other embodiments of the invention, the number can be larger or smaller.

In the embodiment of FIG. 3, the laser radiation was irradiated from above into the waveguide 10 in order to produce the spatial regions 41. As a result, the material of the cladding 12 is also modified in the beam path in such a way that it has a higher etching rate than the unexposed material of the cladding 12 during wet or dry chemical etching, e.g. by means of an aqueous solution of hydrogen fluoride. This creates periodic holes 220 in the material of the cladding 12, which can have a funnel-like shape.

The first longitudinal portion 21, in which the material of the cladding 12 is removed, therefore coincides with the longitudinal extension of the Bragg grating 4 and thus with the expansion of the second longitudinal portion 22. Furthermore, it should be noted that the material of the cladding 12 is not fully removed in the first longitudinal portion 21 due to the selective etching of the exposed spatial regions and that the cladding merely has periodic holes 220.

FIG. 3 and FIG. 4 also show clusters of nanoparticles 3, which are preferably arranged in the holes 220. The holes 220 allow a control of the size of the clusters, as a result of which the wavelength of the plasmon resonance can be adjusted when the device is produced. The more nanoparticles 3 are available in a cluster in a hole 220, the larger is the wavelength of the plasmon resonance.

The nanoparticles 3 can further be functionalized in all the described embodiments of the invention, e.g. by the attachment of antibodies, as a result of which the presence of antigens can be identified and/or quantified by means of the optical losses occurring in the waveguide.

In some embodiments of the invention, the core 11 can contain, in addition to the illustrated Bragg grating 4, further Bragg gratings, by means of which the temperature, the mechanical stress or the form of the waveguide 10 can be determined.

FIGS. 5, 6 and 7 explain the determination of the refractive index of a fluid, i.e. of a gaseous or liquid medium, which surrounds a sensor according to any of FIGS. 1 to 4.

As already obvious, the Bragg wavelength changes in accordance with the index of refraction of the medium surrounding the waveguide 10, as shown in FIG. 5 as a comparative example. FIG. 5 shows the standardized intensity of the light reflected by the Bragg grating on the ordinate and its wavelength on the abscissa. Measured values are shown for seven different media having seven different indices of refraction. The measured values were recorded by a known fiber-optic sensor, the surface of which does not contain any nanoparticles.

FIG. 5 shows that the maximum of the reflected light and/or the Bragg wavelength shifts to larger wavelengths when the refractive index is higher. In FIG. 7, the intensity change is plotted on the ordinate against the index of refraction on the abscissa (square measured points). The intensity remains almost constant in the case of the known fiber-optic sensor.

FIG. 6 shows the standardized intensity of reflected light on the ordinate against the wavelength on the abscissa for also seven different media having seven different refractive indices. The measured values according to FIG. 6 were obtained by means of a device according to the invention, which contains nanoparticles 3 in the first longitudinal portion 21. This figure clearly shows a decrease in the intensity of the reflected light and/or an increase in the intensity losses in the waveguide 10 with increasing index of refraction. In FIG. 7, the standardized intensity is also plotted on the ordinate against the refractive index on the abscissa (round data points). A linear regression of these measured values is also shown.

FIG. 7 clearly shows the superiority of the device according to the invention, the measured signal of which varies by 60% in the same measurement range of the index of refraction, whereas the known device without nanoparticles merely shows a change in the measured variable by some few percentages. Therefore, the known sensor has to be read out with a considerably higher effort and still supplies more severe measurement errors for the refractive index than the solution according to the invention.

According to the invention, it was also found that the Bragg wavelength changes when the device according to the invention is immersed into a liquid medium and pressure fluctuations, e.g. sound signals, spread in this medium. FIG. 8 shows the Bragg wavelength on the ordinate and the time on the abscissa. During the illustrated measurement time of 60 seconds an ultrasound signal was coupled into the aqueous medium by the device according to the invention for three periods, namely between about 5 seconds and about 10 seconds, between about 19 seconds and about 31 seconds and between about 44 seconds and about 50 seconds. It is clearly shown that the Bragg wavelength shifts to longer wavelengths when ultrasound signals spread in the aqueous medium. Thus, the device according to the invention can be used as a hydrophone in order to detect sound signals in aqueous media, e.g. in seawater.

In another embodiment of the invention, the measurement of pressure fluctuations, e.g. sound signals, can alternatively be done by measuring the intensity of optical signals, as described above. According to the invention, it was found that the pressure fluctuation in the medium results in a periodic, local change in the index of refraction, which can be detected with the sensor according to the invention, as described above.

In some embodiments of the invention, both the intensity and the Bragg wavelength can be detected. Therefore, the sound signal is detected twice, and it is thus possible to render the measured values plausible. As a result, the reliability of the measurement can be increased.

Of course, the invention is not limited to the embodiment shown in the drawings. Therefore, the above description should not be considered limiting but explanatory. The below claims should be comprehended in such a way that a feature mentioned is available in at least one embodiment of the invention. This does not rule out the presence of further features. If the claims and the above description define "first" and "second" features, this designation serves to distinguish two similar features without determining an order.

The invention claimed is:

1. A device for determining a refractive index or a hydrophone, comprising:
   at least one waveguide having a core and a cladding surrounding the core, the cladding being at least partly removed in at least one first longitudinal portion and the core containing in at least one second longitudinal portion at least one fiber Bragg grating, at least one partial area of a surface being provided in the at least one first longitudinal portion with nanoparticles, wherein the nanoparticles contain a metal or an alloy and have a plasmon frequency which corresponds approximately to a resonance frequency of the at least one fiber Bragg grating; and
   an apparatus for detecting the intensity of light reflected by the at least one fiber Bragg grating.

2. The device or the hydrophone of claim 1, wherein the second longitudinal portion forms at least part of the first longitudinal portion.

3. The device or the hydrophone of claim 1, wherein periodic holes are present in the cladding adjacent to the at least one fiber Bragg grating.

4. The device or the hydrophone of claim 1, wherein the waveguide is made as a single mode fiber.

5. The device or the hydrophone of claim 3, wherein the holes contain clusters of nanoparticles.

6. The device or the hydrophone of claim 1, wherein the nanoparticles contain, or consist of, palladium.

7. The device or the hydrophone of claim 1, wherein at least one partial area of the surface provided with nanoparticles in the first longitudinal portion additionally carries antibodies.

8. The device or the hydrophone of claim 1, further containing at least one laser light source, the emission wavelength of which corresponds approximately to the Bragg wavelength of the at least one fiber Bragg grating, and at least one photodiode which is configured to receive light reflected by the at least one fiber Bragg grating.

9. The device or the hydrophone of claim 1, wherein the first longitudinal portion has a length of about 0.1 mm to about 5.0 mm.

10. The device or the hydrophone of claim 1, further containing an apparatus for detecting the wavelength of the light reflected by the at least one fiber Bragg grating.

11. A method for determining a refractive index or a pressure change of a fluid, which uses at least one waveguide having a core and a cladding surrounding the core, the cladding being at least partly removed in at least one first longitudinal portion and the core in at least one second longitudinal portion containing at least one fiber Bragg grating, wherein at least one partial area of a surface in the at least one first longitudinal portion is provided with nanoparticles, wherein the nanoparticles contain a metal or an alloy and have a plasmon frequency which corresponds approximately to a resonance frequency of the at least one fiber Bragg grating, the method comprising:
   coupling light into the core of the waveguide; and
   determining at least one of the refractive index or the pressure change from the intensity of light reflected by the at least one fiber Bragg rating.

12. The method of claim 11, wherein at least one of antigens or viruses are also identified by additionally providing at least one partial area of a surface of the core in the first longitudinal portion with antibodies.

13. The method of claim 11, wherein laser light is coupled into the core of the waveguide, the wavelength of which approximately corresponds to the Bragg wavelength of the at least one fiber Bragg grating.

14. A method for producing a device for determining a refractive index or a hydrophone that includes at least one waveguide having a core and a cladding surrounding the core, the cladding being at least partly removed in at least one first longitudinal portion and the core containing in at least one second longitudinal portion at least one fiber Bragg grating, at least one partial area of a surface being provided in the first longitudinal portion with nanoparticles, wherein the nanoparticles contain a metal or an alloy and have a plasmon frequency which corresponds approximately to a resonance frequency of the at least one fiber Bragg grating, wherein the device or the hydrophone further comprises an apparatus for detecting the intensity of light reflected by the at least one fiber Bragg grating wherein the method comprises: producing the at least one fiber Bragg grating in the core of a waveguide having a core and a cladding surrounding the core by point-to-point exposure with laser radiation; removing the cladding of the waveguide n at least partly rcmovcd by wet or dry chemical etching; and providing at least one partial area of a surface of the core with the nanoparticles.

15. The method of claim 13, wherein an aqueous solution of hydrogen fluoride is used for etching and periodic holes are etched into the cladding adjacent to the at least one fiber Bragg grating.

16. The method of claim 13, wherein the nanoparticles are activated by a plasma.

17. The method of claim 13, wherein the nanoparticles are deposited in periodic holes in clusters.

18. The method of claim 13, wherein the wavelength of the light reflected by the at least one fiber Bragg grating is additionally determined.

* * * * *

UNITED STATES PATENT AND TRADEMARK OFFICE
CERTIFICATE OF CORRECTION

PATENT NO. : 10,184,888 B2
APPLICATION NO. : 15/515958
DATED : January 22, 2019
INVENTOR(S) : Wolfgang Schade et al.

Page 1 of 1

It is certified that error appears in the above-identified patent and that said Letters Patent is hereby corrected as shown below:

In the Specification

At Column 1, Line 15, insert the following section in front of "TECHNICAL FIELD":
--GOVERNMENT LICENSE RIGHTS
This invention was made with government support under Grant No. DE-SC0010679 awarded by the Department of Energy. The government has certain rights in the invention.--

Signed and Sealed this
Fifth Day of January, 2021

Andrei Iancu
*Director of the United States Patent and Trademark Office*